(12) United States Patent
Douseki et al.

(10) Patent No.: US 11,523,945 B2
(45) Date of Patent: Dec. 13, 2022

(54) DEVICE FOR ASSESSING NEED TO REPLACE ABSORBENT MEMBER

(71) Applicants: The Ritsumeikan Trust, Kyoto (JP); ABLIC Inc., Chiba (JP)

(72) Inventors: Takakuni Douseki, Kusatsu (JP); Ami Tanaka, Kusatsu (JP); Ryota Suematsu, Kusatsu (JP); Hiroya Sakamoto, Kusatsu (JP)

(73) Assignees: The Ritsumeikan Trust, Kyoto (JP); ABLIC Inc., Chiba (JP)

( * ) Notice: Subject to any disclaimer, the term of this patent is extended or adjusted under 35 U.S.C. 154(b) by 848 days.

(21) Appl. No.: 16/344,404

(22) PCT Filed: Oct. 26, 2017

(86) PCT No.: PCT/JP2017/038790
§ 371 (c)(1),
(2) Date: Apr. 24, 2019

(87) PCT Pub. No.: WO2018/079680
PCT Pub. Date: May 3, 2018

(65) Prior Publication Data
US 2020/0046573 A1     Feb. 13, 2020

(30) Foreign Application Priority Data
Oct. 28, 2016     (JP) .............................. JP2016-212102

(51) Int. Cl.
*A61F 13/42*     (2006.01)
(52) U.S. Cl.
CPC ........ *A61F 13/42* (2013.01); *A61F 2013/424* (2013.01); *A61F 2013/425* (2013.01); *A61F 2013/426* (2013.01)

(58) Field of Classification Search
CPC ................ A61F 13/42; A61F 2013/424; A61F 2013/425; A61F 2013/426
See application file for complete search history.

(56) References Cited

U.S. PATENT DOCUMENTS 7,700,821 B2     4/2010   Ales, III et al.
2011/0095884 A1*   4/2011   Xu .......................... A61F 13/42
                                                            340/539.11
(Continued)

FOREIGN PATENT DOCUMENTS

CN     101790361 A    7/2010
JP     S62-134565 A   6/1987
(Continued)

OTHER PUBLICATIONS

Tanaka, Ami et al., "Wearable Self-Powered Diaper-Shaped Urinary-Incontinence Sensor Suppressing Response-Time Variation With 0.3 V Start-Up Converter," IEEE Sensors Journal, vol. 16, No. 10, May 15, 2016, pp. 3472-3479.
(Continued)

*Primary Examiner* — Catharine L Anderson
(74) *Attorney, Agent, or Firm* — Faegre Drinker Riddle & Reath LLP

(57) ABSTRACT

This replacement necessity assessment apparatus for an absorbent member includes: a power generator which is configured to generate power as a result of contact with liquid absorbed in the absorbent member, and of which power generation amount changes in accordance with an amount of the liquid; a signal output unit configured to output a detection signal according to the power generation amount; and a processing unit configured to acquire a parameter regarding the amount of the liquid based on the detection signal, the processing unit configured to deter-
(Continued)

mine, based on the parameter, whether or not replacement of the absorbent member is necessary.

19 Claims, 15 Drawing Sheets

(56) References Cited

U.S. PATENT DOCUMENTS

| | | | | |
|---|---|---|---|---|
| 2012/0268278 | A1* | 10/2012 | Lewis | G16H 40/63 340/573.5 |
| 2014/0327546 | A1* | 11/2014 | Carney | A61F 13/42 340/573.5 |
| 2014/0350502 | A1* | 11/2014 | Berland | A61F 13/42 604/385.01 |
| 2017/0258643 | A1* | 9/2017 | Xu | A61F 13/42 |

FOREIGN PATENT DOCUMENTS

| | | |
|---|---|---|
| JP | 2004-333208 A | 11/2004 |
| JP | 2010-537695 A | 12/2010 |
| JP | 2013-132518 A | 7/2013 |
| JP | 2015-229003 A | 12/2015 |
| JP | 2016-93209 A | 5/2016 |
| WO | WO 2009/027871 A1 | 3/2009 |

OTHER PUBLICATIONS

CN Office Action dated Nov. 18, 2020 that issued in Application 201780066051.6 including English translation.

* cited by examiner

DEVICE FOR ASSESSING NEED TO REPLACE ABSORBENT MEMBER

TECHNICAL FIELD

The present invention relates to a replacement necessity assessment apparatus and the like for an absorbent member which is provided in a disposable diaper, excretion training pants, an incontinence brief, an absorbent pad, or the like, and of which replacement becomes necessary when leakage of absorbed liquid has occurred.

BACKGROUND ART

For example, there are cases where a disposable diaper is used in order to reduce the burden of care for urination of a person who has cognitive impairment or physical handicap (care receiver). In the disposable diaper a water-absorbable member made of a polymer water-absorbable body or the like is provided, and the water-absorbable member absorbs urine, thereby preventing leakage to the outside. However, when the water-absorbable member is saturated with urine, the water-absorbable member can no longer absorb urine, and thus, a caregiver needs to frequently examine the inside of the disposable diaper, to assess the absorption state of urine. Such examination of the absorption state of urine by the caregiver is an act that requires much work, and in addition, could be an act that causes mental pain to a care receiver such as the dignity of the care receiver being impaired, and the like.

As a technology that can solve the above problem, Patent Literature 1 proposes a liquid detection system that includes: a sensor structure having a detection section which detects liquid and a power generation section which generates power using the liquid as a catalyst; and a liquid detection apparatus which detects the liquid based on an output signal from the sensor structure (hereinafter, also referred to as prior art 1). In this liquid detection system, when the sensor structure incorporated in a disposable diaper gets wet with urine, the power generation section generates power, and the detection section is driven by the power. The detection section includes a piezoelectric element which provides a signal caused by piezoelectric generation upon contact with urine, and the output signal of the piezoelectric element is transmitted to the liquid detection apparatus. The liquid detection apparatus acquires the detection time and the amount of urine by analyzing the output signal of the piezoelectric element. It is therefore possible to assess necessity for replacement of the disposable diaper based on the detection time and the amount of urine, and it is possible to eliminate the act by a caregiver of directly examining the disposable diaper worn by a care receiver.

Patent Literature 2 and Non Patent Literature 1 each disclose a disposable diaper provided with an electromotive module which generates electromotive force by coming into contact with urine, and a wireless transmission module which transmits a radio signal (hereinafter, also referred to as prior art 2). The electromotive module includes a pair of electrodes which generate electromotive force with use of urine as an electrolytic solution, and the wireless transmission module transmits, to a receiver, a signal based on the electromotive force of the electromotive module. The signal based on the electromotive force allows detection that urination has occurred, and it is possible to eliminate the act by a caregiver of directly examining the disposable diaper worn by a care receiver.

CITATION LIST

Patent Literature

Patent Literature 1: Japanese Laid-Open Patent Publication No. 2013-132518
Patent Literature 2: Japanese Laid-Open Patent Publication No. 2015-229003

Non Patent Literature

Non Patent Literature 1: Ami Tanaka, Fumiyasu Utsunomiya, Takakuni Douseki, "Wearable Self-Powered Diaper-Shaped Urinary-Incontinence Sensor Suppressing Response-Time Variation with 0.3V Start-Up Converter", IEEE SENSORS JOURNAL VOL. 16, No. 10, May 15, 2016

SUMMARY OF INVENTION

Technical Problem

In the prior art 1 above, the power generator which generates power by use of liquid, and the detector which detects the liquid and provides a detection signal are individually given. Accordingly, the structure may become complicated as the number of components increases.

Meanwhile, in the case of the prior art 2, since urination can be detected by a signal based on electromotive force generated by the electromotive module, the electromotive module can operate both as a power generator and a detector. Unlike the prior art 1 the detector disposed separately from the power generator is not required, the apparatus can be simplified and downsized, and in addition, can be easily incorporated into a disposable diaper or the like.

However, in the prior art 2, it is only possible to detect occurrence of urination. Since a disposable diaper can absorb urine a plurality of times if the amount of urine in each urination is small, replacing the disposable diaper upon detection of a single urination could be uneconomical. In contrast, if a disposable diaper is planned to be replaced after a plurality of times of urination, the possibility increases that the water-absorbable member is saturated with urine before replacement and the urine leaks to the outside.

In addition, not limited to disposable diapers, acquisition of information about the amount of liquid absorbed in an absorbent member is useful for grasping the state of the absorbent member.

An object of the present disclosure is to provide a replacement necessity assessment apparatus for an absorbent member and a method which can not only detect that liquid has been absorbed in the absorbent member but also assess necessity for replacement of the absorbent member. Another object of the present disclosure is to allow acquisition of information about the amount of liquid absorbed in an absorbent member.

Solution to Problem (1) A replacement necessity assessment apparatus for an absorbent member of the present disclosure includes:
a power generator configured to generate power by contact with liquid absorbed in the absorbent member, and of which power generation amount changes in accordance with an amount of the liquid;
a signal output unit configured to output a detection signal according to the power generation amount; and a processing unit configured to acquire a parameter regarding the amount of the liquid based on the detection signal, and configured to assess whether or not replacement of the absorbent member is necessary based on the parameter.

The replacement necessity assessment apparatus having the above configuration can detect that liquid has been absorbed in the absorbent member based on the detection signal according to the power generation amount. By using the parameter regarding the amount of the acquired liquid based on the detection signal, it is possible to assess necessity for replacement based on the amount of the liquid absorbed in the absorbent member. It should be noted that the replacement of the absorbent member encompasses not only replacement of the absorbent member as a single body, but also replacement of the entirety of the article in which the absorbent member is built in as in the case of a disposable diaper.

(2) Preferably, the parameter includes the number of times the liquid has been infused into the absorbent member.

The greater the number of times the liquid is infused into the absorbent member is, the larger the amount of the liquid absorbed in the absorbent member becomes, and thus, the possibility of occurrence of leakage increases due to saturation of the absorbent member. It is therefore possible to assess necessity for replacement at a timing before leakage occurs by the acquisition of the number of times the liquid has been infused into the absorbent member as a parameter. Here, "infuse" means to put (supply) liquid into an absorbent member such that the liquid is absorbed into the absorbent member, from a position close to the absorbent member or a position away from the absorbent member; and encompasses a form in which urination is performed to an absorbent member provided in a disposable diaper or the like. "Infuse" may be replaced with "load". "Load" means to put liquid such that the liquid is absorbed into the absorbent member, from a position close to the absorbent member or a position away from the absorbent member.

(3) The parameter may include an amount of the liquid per infusion that has been infused into the absorbent member.

The amount of the liquid per infusion that is infused into the absorbent member influences the degree of absorption into the absorbent member. For example, comparing a case where a small amount of liquid is infused a large number of times with a case where a large amount of liquid is infused a small number of times, the degrees of absorption may be different from each other even when the total amount of liquid is the same, and leakage may occur earlier in the former case than in the latter case. By acquisition of the amount of liquid per infusion as a parameter, necessity for replacement of the absorbent member can be more appropriately assessed.

(4) Preferably, the signal output unit intermittently outputs the detection signal at a time interval according to the power generation amount, and the processing unit acquires the parameter based on the time interval at which the detection signal is outputted.

Since the time interval at which the detection signal is provided depends on the power generation amount, and the power generation amount depends on the amount of the liquid absorbed in the absorbent member, the parameter regarding the amount of the liquid can be easily acquired based on the time interval at which the detection signal is provided.

(5) Preferably, based on change in the time interval at which the detection signal is outputted, the processing unit acquires, as the parameter, the number of times the liquid has been infused into the absorbent member.

According to this configuration, since change in the time interval at which the detection signal is provided depends on change in the power generation amount, and the change in the power generation amount depends on change in the amount of the liquid absorbed in the absorbent member, based on the change in the time interval at which the detection signal is provided, it is possible to acquire the parameter regarding the change in the amount of the liquid absorbed in the absorbent member, i.e., the timing at which the liquid has been infused into the absorbent member and the number of times of the infusion. The greater the number of times the liquid is infused into the absorbent member is, the larger the amount of the liquid absorbed in the absorbent member becomes, and thus, the possibility of occurrence of leakage increases due to saturation of the absorbent member. It is therefore possible to assess necessity for replacement at a timing before leakage occurs by the acquisition of the number of times the liquid has been infused into the absorbent member as a parameter.

(6) Preferably, based on the time interval at which the detection signal is outputted, the processing unit acquires, as the parameter, an amount of the liquid per infusion that has been infused into the absorbent member.

As described above, since the amount of the liquid per infusion that is infused into the absorbent member influences the degree of absorption into the absorbent member, necessity for replacement of the absorbent member can be more appropriately assessed by the acquisition of the amount of the liquid per infusion as a parameter, together with the number of times the liquid has been infused into the absorbent member.

(7) Preferably, the processing unit acquires the parameter based on an average of the time interval at which the detection signal is outputted.

With this configuration, the parameter can be acquired in a condition where influences of inappropriate variations of the time interval and the like are reduced.

(8) Preferably, the time interval at which the detection signal is outputted is associated with the amount of the liquid for each predetermined range.

With this configuration, the resolution at the time of acquisition of the amount of the liquid can be set as desired.

(9) Preferably, the predetermined range is different in accordance with the number of times of infusion of the liquid into the absorbent member.

When the number of times of infusion of the liquid into the absorbent member is small, the amount of the absorbed liquid is also small. Hence power generation by the power generator tends to be unstable, and the time interval at which the detection signal is provided also tends to be unstable when compared with a case where the number of times of infusion of the liquid is large. Accordingly, if the predetermined range of the time interval is made different in accordance with the number of times of infusion of the liquid, the amount of the liquid can be appropriately associated with the number of times of infusion.

(10) Preferably, the replacement necessity assessment apparatus further includes: a radio transmitter configured to wirelessly transmit the detection signal; and a radio receiver configured to receive the detection signal transmitted, wherein the processing unit acquires the parameter based on the detection signal received by the radio receiver.

With this configuration, the power generator and the signal output unit can be disposed away from the processing unit. Thus, for example, at a place away from the person who is wearing the diaper provided with the absorbent member, necessity for replacement can be assessed.

(11) Preferably, at a previous stage corresponding to a number of times before the number of times of infusion of the liquid that requires replacement of the absorbent member, the processing unit assesses necessity for replacement of the absorbent member at a subsequent infusion or thereafter.

With this configuration, when infusion of the liquid that could cause leakage has been performed, it is possible to immediately make notification or the like that replacement is necessary, without acquiring the amount and the like of the urine.

(12) Preferably, the power generator includes a sheet-shaped electrode that consists only of carbon or a sheet-shaped electrode that contains the carbon.

With this configuration, it is possible to obtain desired power generation characteristics such that the power generation amount changes in accordance with the amount of the liquid.

(13) Preferably, the sheet-shaped electrode is disposed at a side opposite to a side where the liquid is infused into the absorbent member.

(14) An apparatus of the present disclosure includes:

a power generator configured to generate power as a result of contact with liquid absorbed in an absorbent member, and of which power generation amount changes in accordance with an amount of the liquid; and a signal output unit configured to intermittently output a detection signal at a time interval according to the power generation amount.

In the apparatus having the above configuration, since the power generator is constituted such that the power generation amount changes in accordance with the amount of the liquid absorbed in the absorbent member, and the signal output unit intermittently provides the detection signal at a time interval according to the power generation amount, it is possible to acquire information about the amount of the liquid absorbed in the absorbent member, by use of the time interval at which the detection signal is provided.

The above "absorbent member" is not limited to those of which replacement is necessary or of which replacement can be performed. For example, the absorbent member is not limited to those applied to disposable diapers, water-absorbable pads, and the like, but encompasses anything that can absorb liquid. For example, the absorbent member encompasses plants that absorb water from the ground, or culture media with which plants are cultured. In this case, the amount of the liquid inside the plant or the culture medium can be grasped, and the apparatus can be utilized in determining the timing or the like at which water or culture liquid is supplied.

The "information about the amount of the liquid" can include the amount (total amount) itself of the liquid absorbed in the absorbent member, or a predetermined parameter regarding the amount of the liquid. Examples of the parameter include the number of times the liquid has been infused into the absorbent member, and the amount of the liquid per infusion that has been infused into the absorbent member.

(15) The apparatus further includes a processing unit configured to acquire a parameter regarding the amount of the liquid based on the time interval at which the detection signal is outputted.

According to this configuration, by using the parameter regarding the amount of the liquid that has been acquired based on the time interval at which the detection signal is provided, it is possible to grasp the amount of the liquid absorbed in the absorbent member.

Advantageous Effects of Invention

According to the replacement necessity assessment apparatus for the absorbent member of the present disclosure, it is possible to not only detect that the liquid has been infused into the absorbent member, but also assess necessity for replacement of the absorbent member. According to the apparatus of the present disclosure, information about the amount of the liquid absorbed in the absorbent member can be acquired.

DESCRIPTION OF EMBODIMENTS

Hereinafter, embodiments of the present invention will be described.

Figure 1:
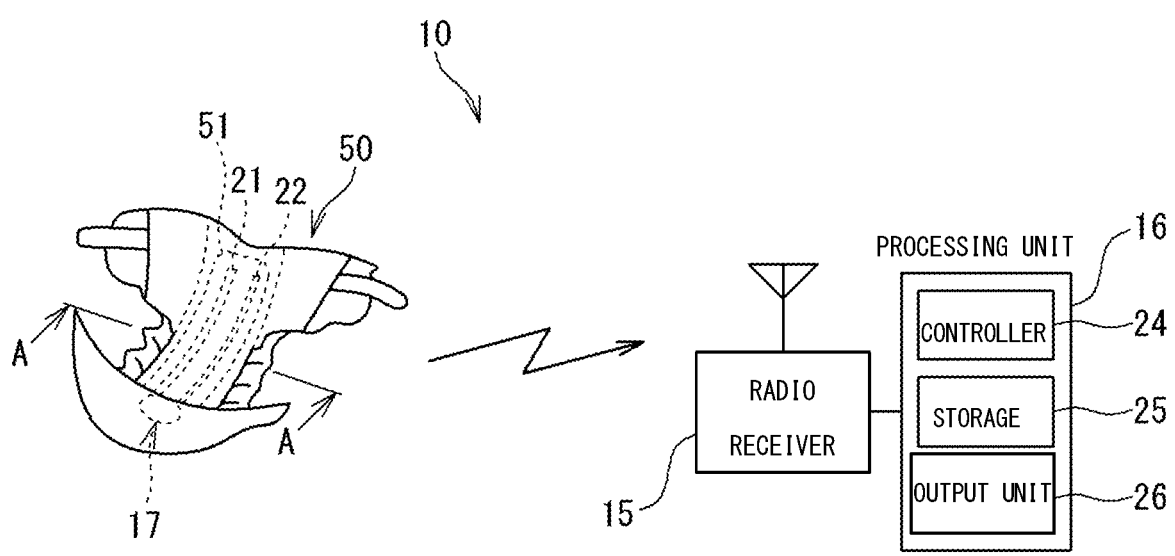
FIG. 1 is a schematic configuration diagram of a replacement time assessment apparatus for an absorbent member according to one embodiment of the present invention.

FIG. 1 is a schematic configuration diagram of a replacement necessity assessment apparatus for an absorbent member according to one embodiment of the present invention.

A replacement necessity assessment apparatus 10 of the present embodiment is applied to a disposable diaper (hereinafter, simply referred to as "diaper") 50, detects urination in the diaper 50, and assess necessity for replacement or the replacement time of the diaper 50 based on the amount of urine or the like.

The diaper 50 exemplified in FIG. 1 is of a so-called open type and is of a type worn by a user such as a care receiver, an infant, or the like and fixed with tape. An absorbent member 51 made from a polymer absorber, cotton-like pulp, or the like is disposed in the diaper 50. The absorbent member 51 can absorb urine. The absorbent member 51 also serves as a holder capable of holding the absorbed liquid.
[Configuration of Replacement Necessity Assessment Apparatus]

The replacement necessity assessment apparatus 10 includes a sensor unit 17, a radio receiver 15, and a processing unit 16.

Figure 2:
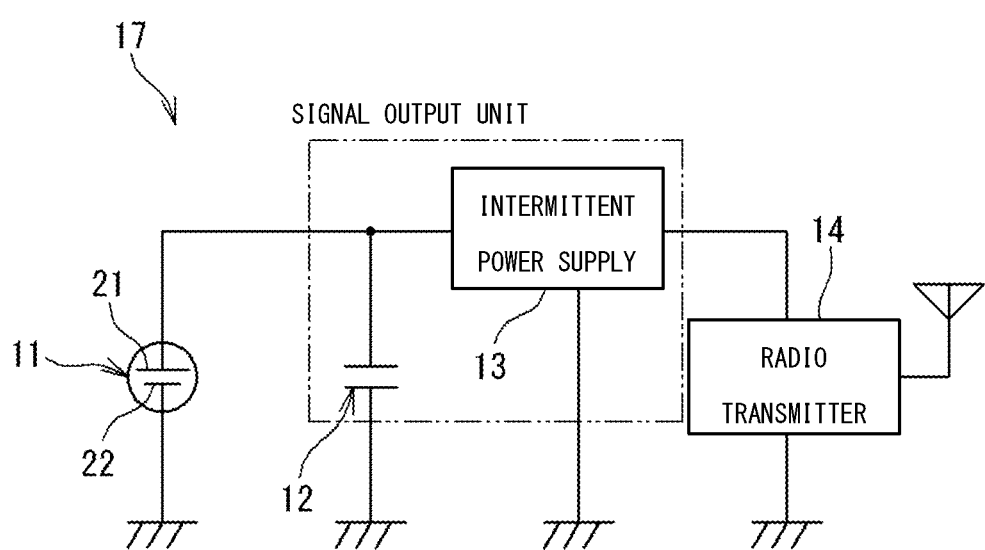
FIG. 2 is a schematic configuration diagram showing a sensor unit.

FIG. 2 is a schematic configuration diagram showing the sensor unit 17. The sensor unit 17 is incorporated in the diaper 50, and includes a power generator 11, a power storage 12, an intermittent power supply 13, and a radio transmitter 14.
(Configuration of Power Generator 11)

Figure 3:
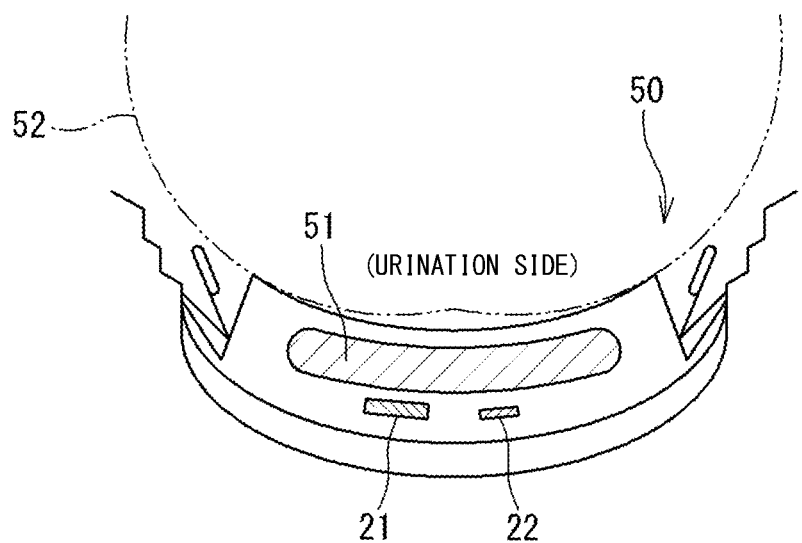
FIG. 3 is a cross-sectional view taken along a line A-A shown in FIG. 1.

FIG. 3 is a cross-sectional view taken along a line A-A shown in FIG. 1.

As shown in FIG. 1 to FIG. 3, the power generator 11 includes a pair of electrodes 21, 22. The pair of electrodes 21, 22 generates electromotive force with use of urine absorbed in the absorbent member 51 as an electrolytic solution. The pair of electrodes 21, 22 is formed to be long, and is arranged apart from each other in the left-right direction and along the front-rear direction of the disposable diaper 50.

The pair of electrodes 21, 22 is constituted as a combination of a sheet-shaped electrode 21 that consists only of carbon or a sheet-shaped electrode 21 that contains carbon, and an electrode 22 that uses aluminum as a material, for example. The carbon applied to the sheet-shaped electrode 21 can include a synthetic resin such as phenol, coal, coke, an activated carbon made from a raw material derived from a fossil fuel such as pitch, or a mesoporous carbon. Each electrode 21, 22 is formed to have a length of 320 mm, for example. One of the electrodes 21 made from carbon is formed to have a width of about 5 mm, and the electrode 22 made from aluminum is formed to have a width of about 2 mm. As shown in FIG. 3, the pair of electrodes 21, 22 is disposed at a lower side relative to the absorbent member 51, i.e., at a side opposite to the side (urination side) that is in contact with a person 52 wearing the diaper 50. The carbon in the sheet-shaped electrode 21 is porous and can absorb and hold liquid. For example, the carbon in the sheet-shaped electrode 21 has a large number of nano-order pores.

The thickness of the sheet-shaped electrode 21 may be set to 50 to 500 μm, more preferably, 100 to 400 μm. The density of the carbon in the sheet-shaped electrode 21 may be set to 0.3 to 1.0 g/cc, more preferably, 0.4 to 0.7 g/cc. The specific surface area of the carbon in the sheet-shaped electrode 21 may be set to 500 to 4000 $m^2/g$, more preferably, 1000 to 2000 $m^2/g$. The mean particle diameter of the carbon in the sheet-shaped electrode 21 may be set to 0.1 to 10 μm, more preferably, 1 to 5 μm.

The sheet-shaped electrode 21 can be manufactured as follows: for example, a tetrafluoroethylene resin dispersion liquid as a binder and KETJENBLACK as a conductive auxiliary agent are mixed into a predetermined amount of steam-activated activated carbon, the resultant mixture is kneaded, and the kneaded material is stretched into a sheet shape while being pressed by a biaxial roller.

It should be noted that the pair of electrodes 21 is not limited to those made from the above materials or by the above manufacturing method, and the pair of electrodes 21 is not particularly limited as long as the pair of electrodes 21 has the power generation characteristics described later.
(Configuration of Power Storage 12 and Intermittent Power Supply 13)

As shown in FIG. 2, the power storage 12 is implemented as a capacitor (condenser). Electromotive force generated by the power generator 11 is applied to the power storage 12, and electric charge is stored therein. When a predetermined amount of electric charge has been stored in the power storage 12, the intermittent power supply 13 receives power as a result of release of the electric charge, and operates. When the electric charge has been released from the power storage 12, electric charge is stored again in the power storage 12, by the power generator 11. Accordingly, in the power storage 12, accumulation (charging) and release (discharging) of electric charge are repeated, and the intermittent power supply 13 intermittently operates every time the power storage 12 discharges.

Every time power is supplied from the power storage 12, the intermittent power supply 13 intermittently generates and provides a detection signal. That is, the power storage 12 and the intermittent power supply 13 form a signal output unit which outputs the detection signal. Since the detection signal provided by the intermittent power supply 13 is generated by the electromotive force that has occurred in association with urination into the absorbent member 51, the detection signal serves as a signal that detects that urination has been performed. The detection signal is provided to the radio transmitter 14, as a source of power.

(Configuration of Radio Transmitter 14 and Radio Receiver 15)

As shown in FIG. 2, the radio transmitter 14 is constituted to transmit to the outside a radio signal having a predetermined amplitude, by receiving the detection signal as the source of power. Since transmission of this radio signal is substantially simultaneous with the supply of the detection signal, the radio signal substantially corresponds to the detection signal.

As shown in FIG. 1, the radio receiver 15 receives the radio signal transmitted from the radio transmitter 14. Then, the radio receiver 15 sends the radio signal to the processing unit 16, as a detection signal.

(Configuration of Processing Unit 16)

The processing unit 16 is constituted from a personal computer, a tablet PC, a smart phone, or the like, for example. The processing unit 16 includes: a controller 24 such as a CPU; a storage 25 such as a memory; and an output unit 26 such as a liquid crystal monitor and a speaker. The processing unit 16 performs a predetermined process regarding replacement of the absorbent member 51 (the diaper 50) based on the detection signal transmitted from the radio receiver 15. The processing unit 16 performs: a process of detecting that urination has been performed, a process of acquiring the number of times of urination, the total amount of urine, and the amount of urine per urination; a process for determining whether or not replacement of the absorbent member 51 is necessary; and the like. These processes are realized by the controller 24 performing software installed in the storage 25. Details of the processes will be described later.

(Power Generation Characteristics of Power Generator 11)

The power generator 11 of the present embodiment has power generation characteristics in which the power generation amount changes in accordance with the amount of urine absorbed in the absorbent member 51 of the diaper 50. Specifically, the power generator 11 has power generation characteristics in which the larger the amount of urine absorbed in the absorbent member 51 is, the larger the power generation amount becomes. In particular, the amount of urine that can be held by the sheet-shaped electrode 21 containing carbon correlates with the amount of urine absorbed in the absorbent member 51. Specifically, the larger the amount of urine absorbed in the absorbent member 51 is, the larger the amount of urine held by the sheet-shaped electrode 21 becomes. The larger the amount of urine held by the sheet-shaped electrode 21 is, the larger the power generation amount also becomes.

Figure 4:
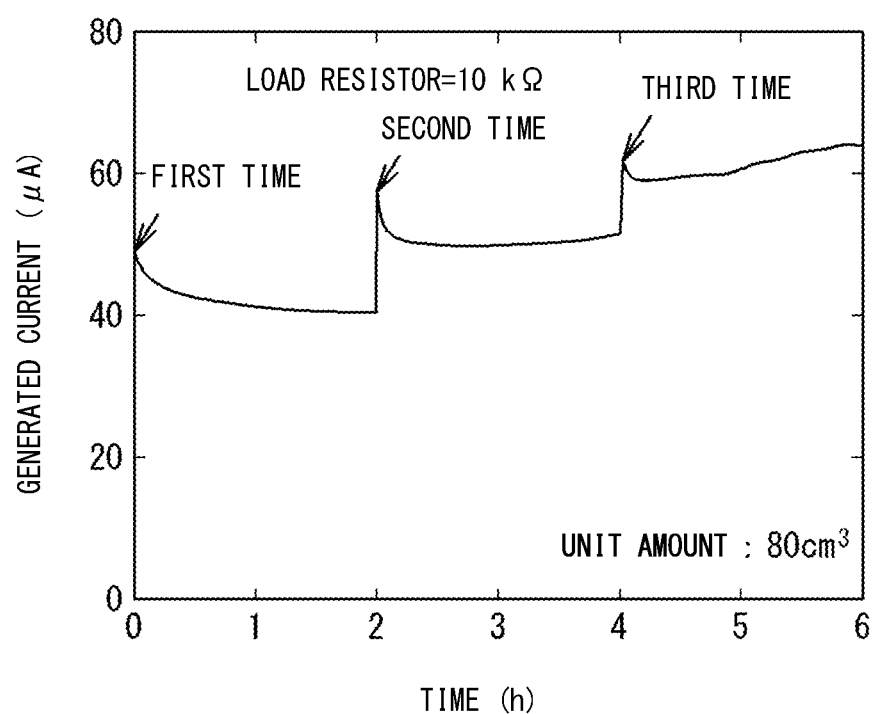
FIG. 4 is a graph showing change, according to the amount of urine, in the value of current generated by a power generator.

FIG. 4 is a graph showing change, according to the amount of urine, in the value of current generated by the power generator 11. The current value was measured by urine being infused (urinated) into the absorbent member 51 of the diaper 50, in a state where a 10 kΩ load resistor is connected in parallel to the pair of electrodes 21, 22. Urine was infused by 80 cm³ every two hours, a plurality of times.

As shown in FIG. 4, when urine has been infused for the first time, the value of the current generated by the power generator 11 rises sharply, then the current value decreases, and then stably stays at a substantially constant value (about 40 μA). When urine has been infused for the second time, the current value rises sharply again, then the current value decreases, and then, stably stays at a substantially constant value (about 50 μA). Thus, the current value that has become stable after the second infusion of urine has a value greater than the current value that has become stable after the first infusion of urine. The minimum value of the current after the third infusion of urine has a value greater than the minimum value of the current after the second infusion of urine. When urine has been infused for the third time, the current value rises sharply again, then, the current value decreases, and then, stably stays at a substantially constant value (about 60 μA). The current value that has become stable after the third infusion of urine has a value greater than the current value that has become stable after the second infusion of urine. The minimum value of the current after the second infusion of urine has a value greater than the minimum value of the current after the first infusion of urine.

As described above, the larger the total amount of urine infused into the absorbent member 51, i.e., the larger the total amount of urine absorbed in the absorbent member 51, is, the larger the power generation amount by the power generator 11 becomes. In other words, the larger the total amount of urine infused into the absorbent member is, the greater the average of the power generation amount in the time period from the infusion of urine into the absorbent member 51 until the next infusion of urine becomes.

(Output of Detection Signal by Intermittent Power Supply 13)

Figure 5A:
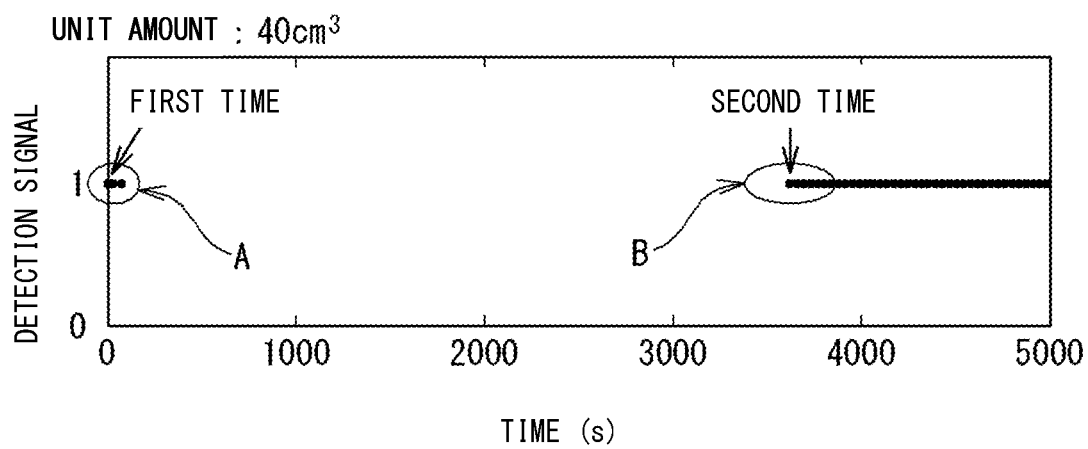
FIG. 5A is a graph obtained by plotting a detection signal received by a radio receiver when a predetermined unit amount (40 $cm^3$) of urine has been infused.
Figure 5B:
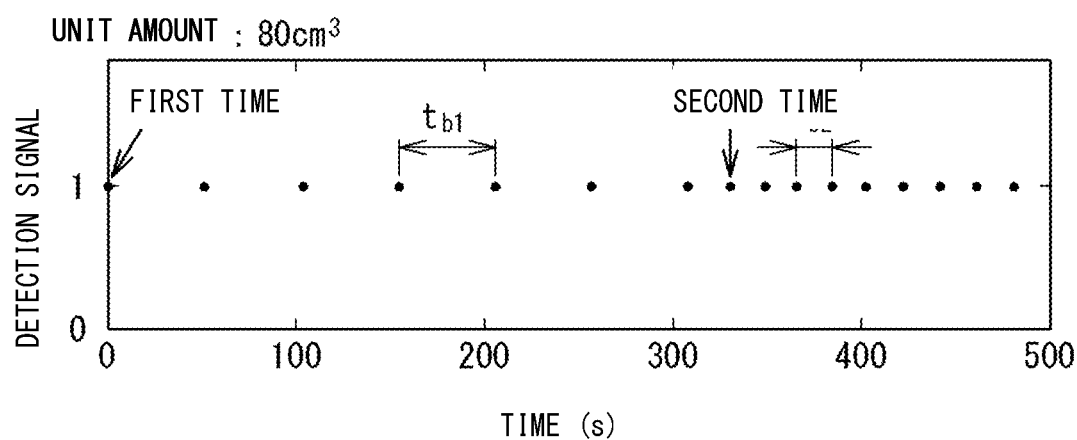
FIG. 5B is a graph obtained by plotting the detection signal received by the radio receiver when a predetermined unit amount (80 $cm^3$) of urine has been infused.
Figure 5C:
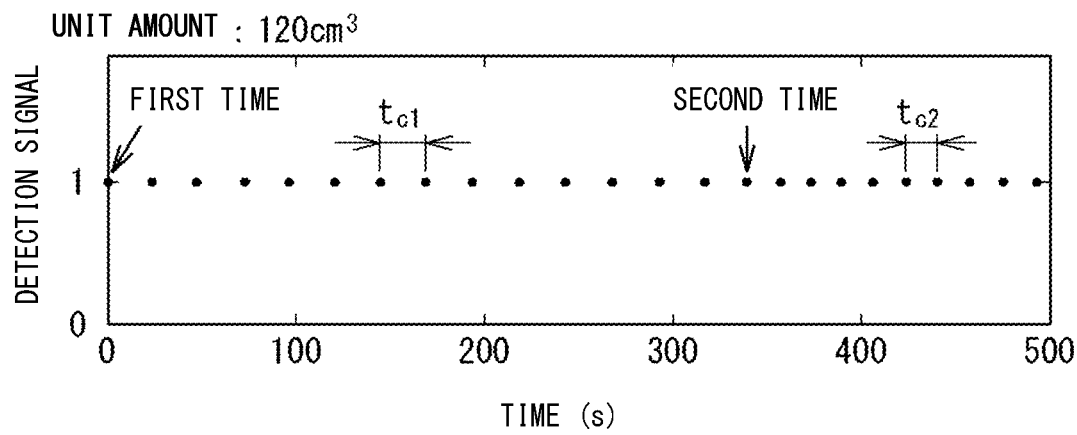
FIG. 5C is a graph obtained by plotting the detection signal received by the radio receiver when a predetermined unit amount (120 $cm^3$) of urine has been infused.
Figure 6A:
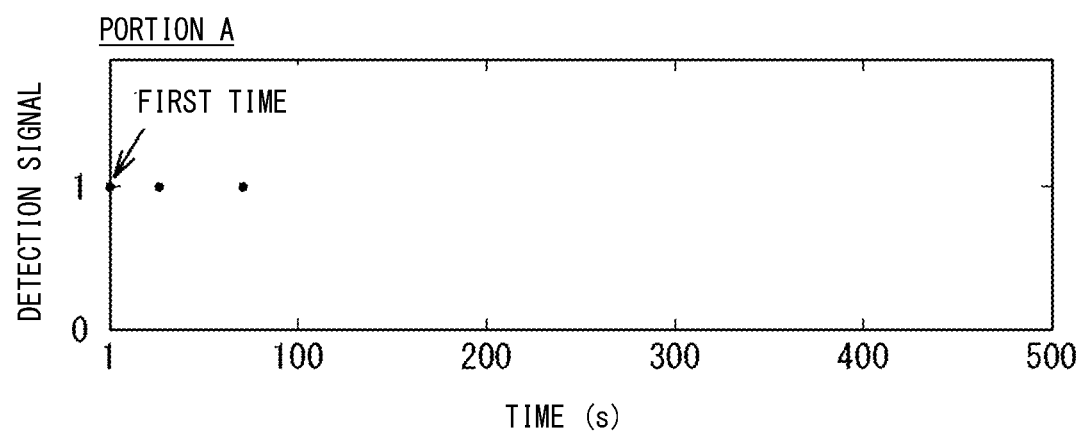
FIG. 6A is a graph showing a portion A in FIG. 5A in an enlarged manner.
Figure 6B:
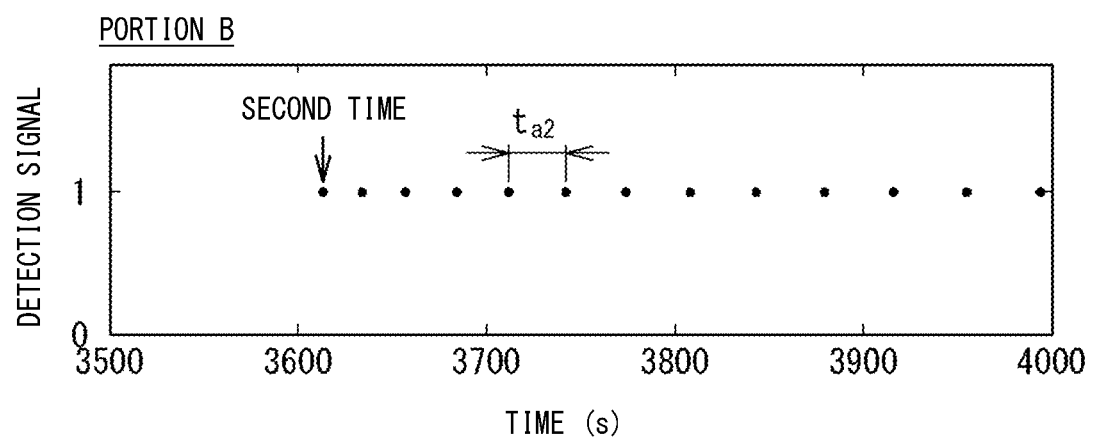
FIG. 6B is a graph showing a portion B in FIG. 5A in an enlarged manner.

FIG. 5A to FIG. 5C are graphs obtained by plotting the detection signal received by the radio receiver 15. The reception timing of the detection signal by the radio receiver 15 can be considered to be substantially simultaneous with the output timing of the detection signal by the intermittent power supply 13. Each of FIG. 5A to FIG. 5C, respectively, shows a case where urine has been infused twice with a time interval therebetween with the unit amount set to 40 cm³, with the unit amount set to 80 cm³, and with the unit amount set to 120 cm³. One division of the horizontal axis of the graph in FIG. 5A is 1000 seconds, and one division of the horizontal axis of the graph in each of FIG. 5B and FIG. 5C is 100 seconds. FIG. 6A and FIG. 6B show graphs of a portion A and a portion B in FIG. 5A, using the same divisions as those in the horizontal axes in FIG. 5B and FIG. 5C.

As shown in FIG. 5A and FIG. 6A, immediately after 40 cm³ of urine has been infused for the first time, several receptions of the detection signal have been confirmed immediately thereafter. However, thereafter, no signal has been received. Then, as shown in FIG. 5A and FIG. 6B, when urine has been infused for the second time after about one hour (3600 seconds), the detection signal has been received at a substantially constant time interval (reception interval) $t_{a2}$. Accordingly, based on the change in the time interval of the received detection signal (reception interval), the timing at which the urine has been infused and the number of times the urine has been infused can be detected.

As shown in FIG. 5B, when 80 cm³ of urine has been infused for the first time, the detection signal has been received at a substantially constant reception interval $t_{b1}$ until the second infusion. As shown in FIG. 5C, when 120 cm³ of urine has been infused for the first time, the detection signal has been received at a substantially constant reception interval $t_{c1}$ until the second infusion. Then, in the respective cases, when urine has been infused for the second time, the detection signal has been received at a time interval $t_{b2}$, $t_{c2}$, which are shorter than those of the first time. Accordingly, similar to the above, the timing at which urine has been infused and the number of times the urine has been infused can be detected based on the change in the reception interval of the detection signal. The number of times the urine has been infused is used in assessment of necessity for replacement of the diaper 50, as described later.

Figure 7A:
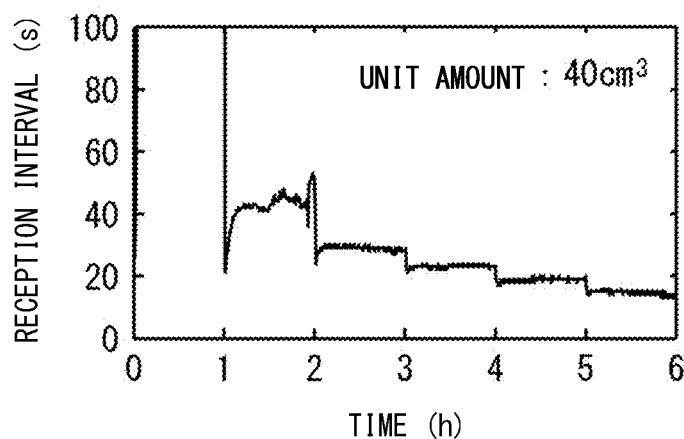
FIG. 7A is a graph showing change in a reception interval of the detection signal when a predetermined unit amount (40 $cm^3$) of urine has been infused every constant time period.
Figure 7B:
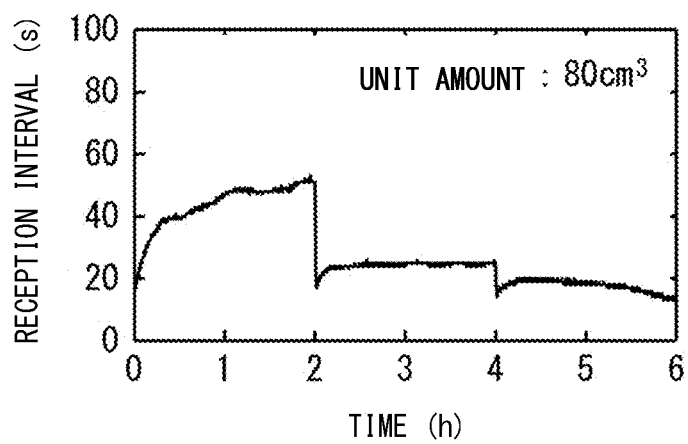
FIG. 7B is a graph showing change in the reception interval of the detection signal when a predetermined unit amount (80 $cm^3$) of urine has been infused every constant time period.
Figure 7C:
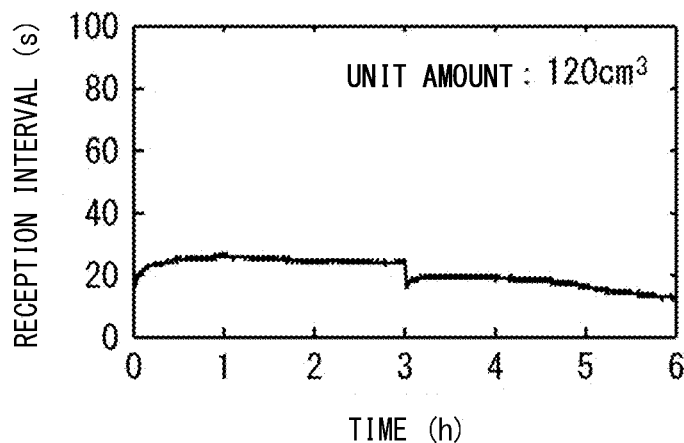
FIG. 7C is a graph showing change in the reception interval of the detection signal when a predetermined unit amount (120 $cm^3$) of urine has been infused every constant time period.

FIG. 7 is a group of graphs each showing change in the reception interval of the detection signal when a predetermined unit amount of urine has been infused every constant time period, wherein the horizontal axis is time and the vertical axis is reception interval of the detection signal. FIG. 7A shows a case where a unit amount of 40 cm$^3$ of urine has been infused every one hour, FIG. 7B shows a case where a unit amount of 80 cm$^3$ of urine has been infused every two hours, and FIG. 7C shows a case where a unit amount of 120 cm$^3$ of urine has been infused every three hours.

As shown in FIG. 7A, in the case where the unit amount is 40 cm$^3$, as described with reference to FIG. 5A, after urine has been infused for the first time, the detection signal has hardly been received, and thus, the reception interval has significantly increased, and appropriate values have been acquired from the second infusion of urine and thereafter. In the time period after the second infusion of urine before the third infusion (one to two hours in the horizontal axis), reception intervals have been about 40 to 50 seconds although slightly unstable. After the third infusion, the detection signal has been received at a substantially constant reception interval. In addition, the larger the total amount of the infused urine is, the shorter the reception interval becomes.

As shown in FIG. 7B, in the case where the unit amount is 80 cm$^3$, after the first infusion of urine, the reception interval has gradually increased and become gradually stable, and after the second infusion of urine, the reception interval has become substantially constant. In addition, the larger the total amount of the infused urine is, the shorter the reception interval becomes.

As shown in FIG. 7C, in the case of the unit amount of 120 cm$^3$, both after the first infusion of urine and after the second infusion, the detection signal has been received at a substantially stable reception interval. In addition, the larger the total amount of the infused urine is, the shorter the reception interval becomes.

As described above, the larger the amount of urine infused and absorbed in the absorbent member 51 is, the shorter the reception interval of the detection signal becomes. This is because, as shown in FIG. 4, the larger the amount of urine infused in the absorbent member 51 is, the larger the power generation amount in the power generator 11 becomes, and in association therewith, the charging speed of the power storage 12 increases, and the operation interval (the output interval of the detection signal) of the intermittent power supply 13 shortens.

Figure 8A:
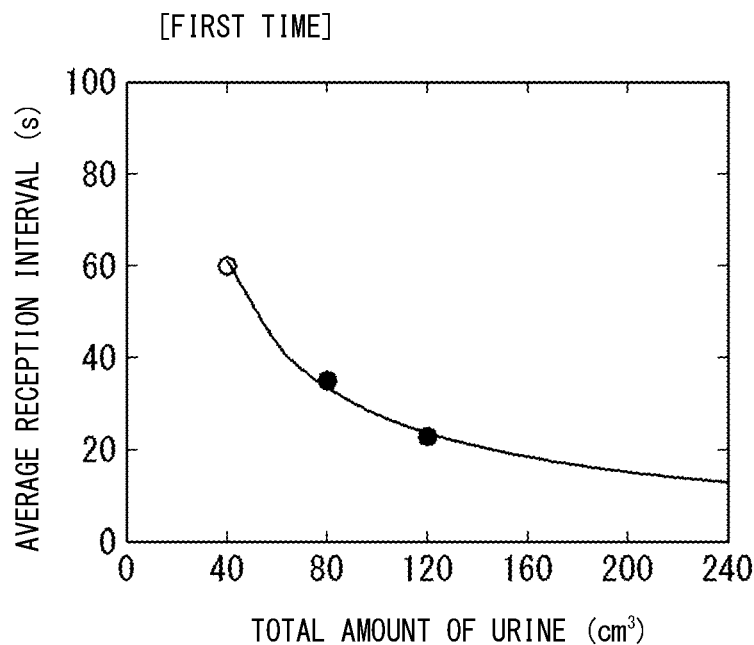
FIG. 8A is a graph showing the relationship between the total amount of urine and the average reception interval when urine has been infused for the first time.
Figure 8B:
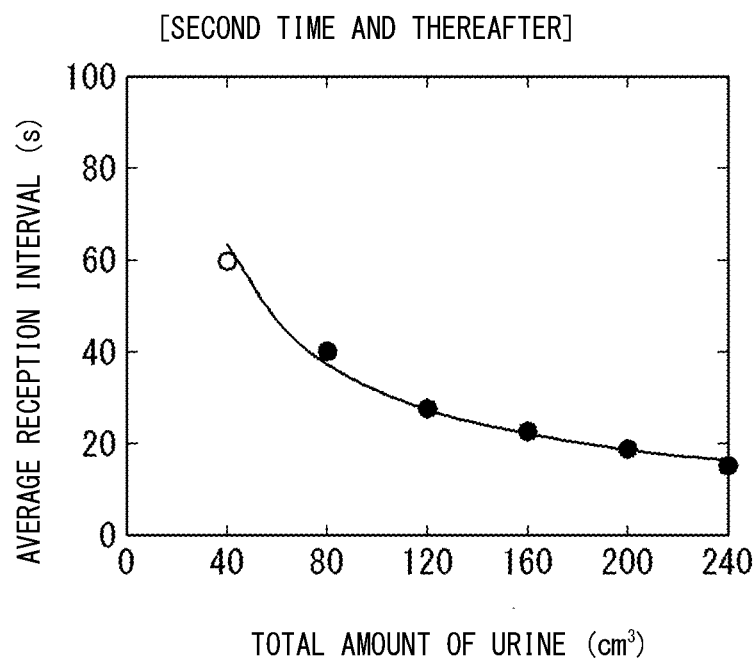
FIG. 8B is a graph showing the relationship between the total amount of urine and the average reception interval when urine has been infused for the second time and thereafter.

Even if the unit amount of infused urine is different, the reception interval becomes substantially the same when the total amount is the same. FIG. 8A and FIG. 8B are graphs each showing the relationship between the total amount of urine and the average reception interval. In particular, FIG. 8A shows a case where urine is infused for the first time, and FIG. 8B shows a case where urine is infused for the second time and thereafter. The reason why the first time is separated from the second time and thereafter is as follows. For example, as shown in FIG. 7A and FIG. 7B, after the first infusion of urine, the variation of the reception interval is large, and after the second infusion of urine and thereafter, the reception interval is stable, and thus, there is a possibility that even if the total amount is the same, the average reception interval is different. It should be noted that, as shown in FIG. 5A, in a case where a unit amount of 40 cm$^3$ of urine is infused for the first time, the detection signal is received immediately after the infusion, but the detection signal is not received thereafter. Thus, in FIG. 8A and FIG. 8B, the average reception interval is assumed to be about 60 seconds.

As shown in FIG. 8A and FIG. 8B, the larger the total amount of urine is, the shorter the average reception interval becomes. The processing unit 16 in the present embodiment takes, into consideration, the relationship between the reception interval and the total amount of urine as shown in FIG. 8A and FIG. 8B, obtains the average reception interval and the total amount of urine through calculation, and uses the obtained results in assessment for replacement time of the diaper 50, which is described later.

(Acquisition of Total Amount of Urine)

The total amount of urine is obtained based on Table 1 below.

TABLE 1

| Total amount | Range of average reception interval | |
|---|---|---|
| of urine | First loading | Second loading and thereafter |
| 40 cm$^3$ | 44 s ≤ t | — |
| 80 cm$^3$ | 28 s ≤ t < 44 s | 32 s ≤ t |
| 120 cm$^3$ | t < 28 s | 25 s ≤ t < 32 s |
| 160 cm$^3$ | — | 21 s ≤ t < 25 s |
| 200 cm$^3$ | — | 18 s ≤ t < 21 s |

In Table 1, in a case where urine has been infused for the first time, it is considered that 40 cm$^3$ of urine has been infused when the reception interval t in seconds satisfies 44≤t. It is considered that 80 cm$^3$ of urine has been infused when the reception interval t in seconds satisfies 28≤t<44. It is considered that 120 cm$^3$ of urine has been infused when the reception interval t in seconds satisfies t<28.

In a case where urine has been infused for the second time and thereafter, it is considered that the total amount of urine is 80 cm$^3$ when the reception interval t in seconds satisfies 32≤t. It is considered that the total amount of urine is 120 cm$^3$ when the reception interval t in seconds satisfies 25≤t<32. Thereafter, in accordance with decrease of the reception interval t, the total amount of urine is increased by 40 cm$^3$. That is, the total amount of urine is associated with a range of the reception interval, which is set with an increment of 40 cm$^3$. In other words, the total amount of urine is acquired at a resolution of 40 cm$^3$. If such a process is performed, compared with a case where the total amount of urine is more finely measured, the process at the time of assessment of necessity for replacement can be simplified, and the calculation load can be reduced. The amount of urine per infusion can be obtained by calculating the difference between the total amount before the infusion of urine and the total amount after the infusion of the urine.

(The Number of Times of Infusion of Urine and the State of Leakage from Absorbent Material)

Figure 9:
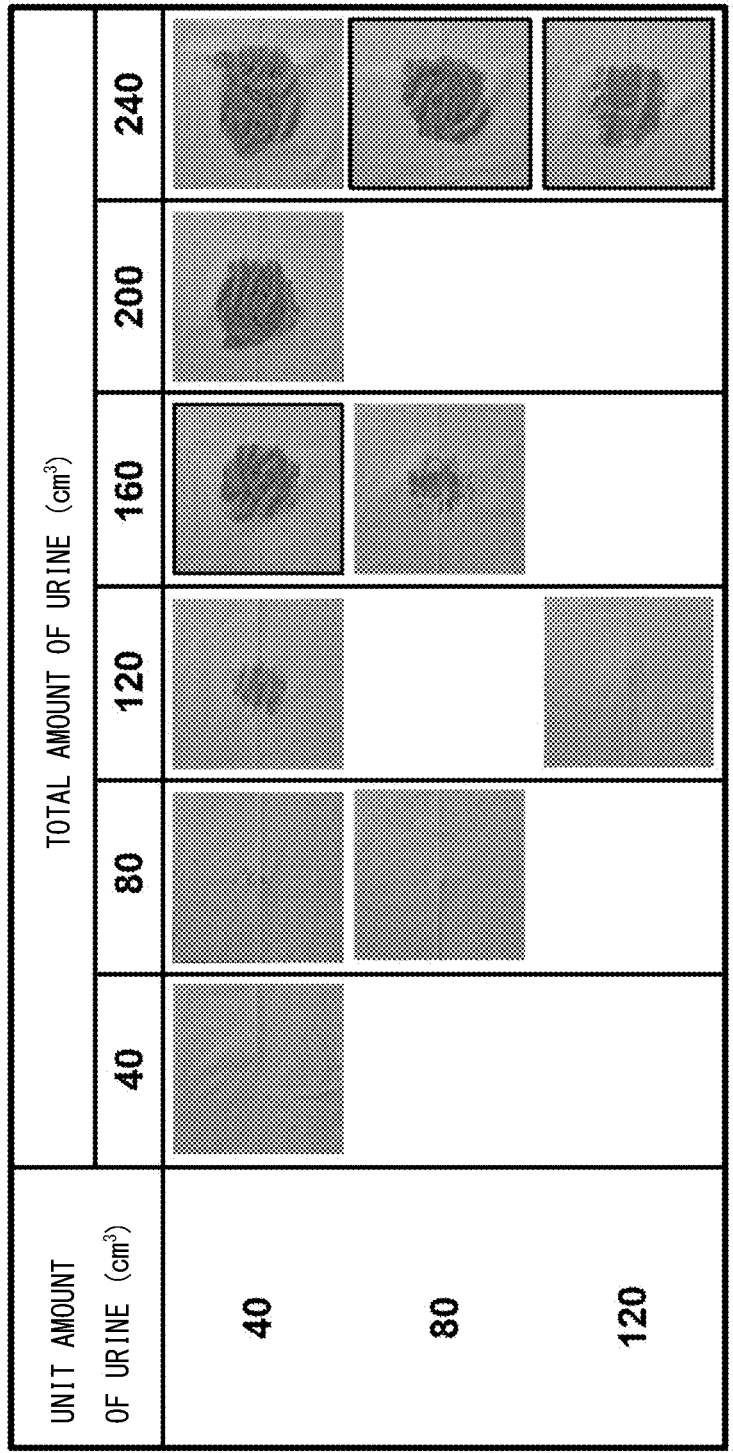
FIG. 9 shows images of the urine leakage state when a unit amount of urine was infused for a plurality of times.

FIG. 9 shows images of the urine leakage state when a unit amount of urine was infused a plurality of times.

When urine has been infused by a unit amount of 40 cm$^3$, a small amount of urine leakage has occurred at the third infusion (total amount: 120 cm$^3$), and a large amount of urine leakage has occurred at the fourth infusion (total amount: 160 cm$^3$). In a case where urine is added by a unit amount of 40 cm$^3$, it can thus be said that replacement of the absorbent member 51 (the diaper 50) becomes necessary at the stage where urine has been infused for the fourth time.

When urine has been infused by a unit amount of 80 cm$^3$, a small amount of urine leakage has occurred at the second infusion (total amount: 160 cm$^3$), and a large amount of urine leakage has occurred at the third infusion (total amount: 240 cm$^3$). It can thus be said that replacement of the absorbent member 51 becomes necessary at the stage where urine has been infused for the third time.

When urine has been infused by a unit amount of 120 cm$^3$, a large amount of leakage has occurred at the second infusion (total amount: 240 cm$^3$). It can thus be said that replacement becomes necessary at the stage where urine has been infused for the second time.

The result shown in FIG. 9 reveals that, even when the total amount is the same, the smaller the unit amount (the amount per infusion) is, the larger the amount of leakage becomes. For example, in the case of the total amount of 120 cm$^3$, a larger amount of leakage has occurred when the unit amount is 40 cm$^3$ than when the unit amount is 120 cm$^3$. In the case of the total amount of 160 cm$^3$, a larger amount of leakage has occurred when the unit amount is 40 cm$^3$ than when the unit amount is 80 cm$^3$. This is because when the unit amount is smaller, urine is less likely to spread on the absorbent member 51 and the urine is absorbed locally at a part of the absorbent member 51. Accordingly, in order to assess necessity for replacement, it is necessary to take not merely the total amount of urine but also the unit amount of urine (the amount of urine per infusion), into consideration.

Figure 10:
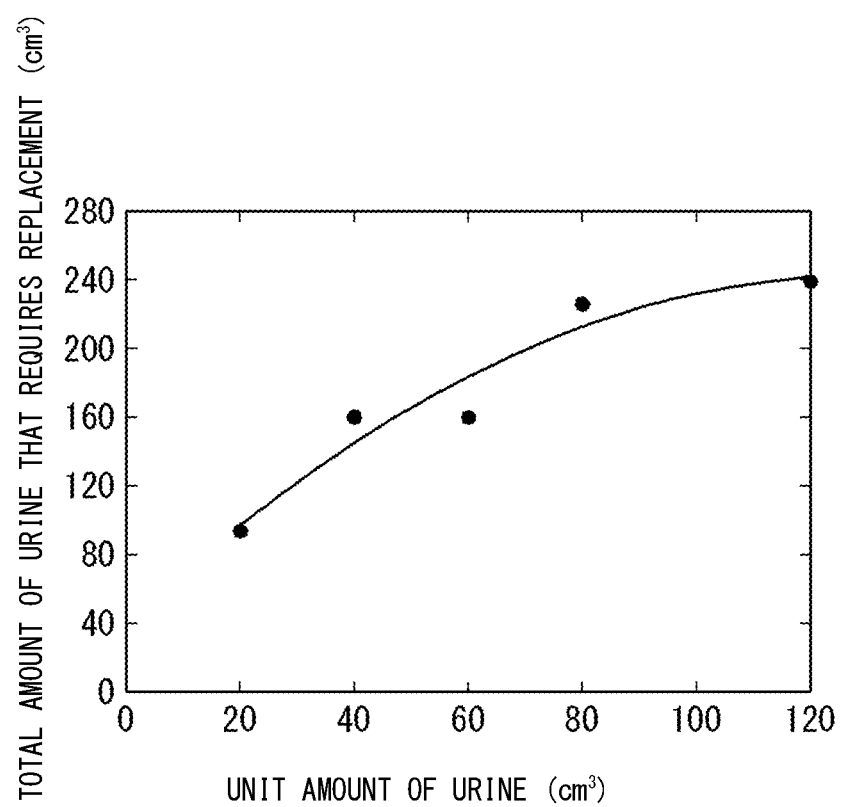
FIG. 10 shows the relationship between the unit amount of urine and the total amount of urine that requires replacement of the absorbent member.

FIG. 10 shows the relationship between the unit amount of urine and the total amount of urine that requires replacement of the absorbent member 51. In the present embodiment, as described below, the replacement time is assessed in consideration of the number of times of urination and the amount of urine per urination.

[Procedure of Process for Assessment of Necessity for Replacement of Absorbent Member 51]

Figure 11:
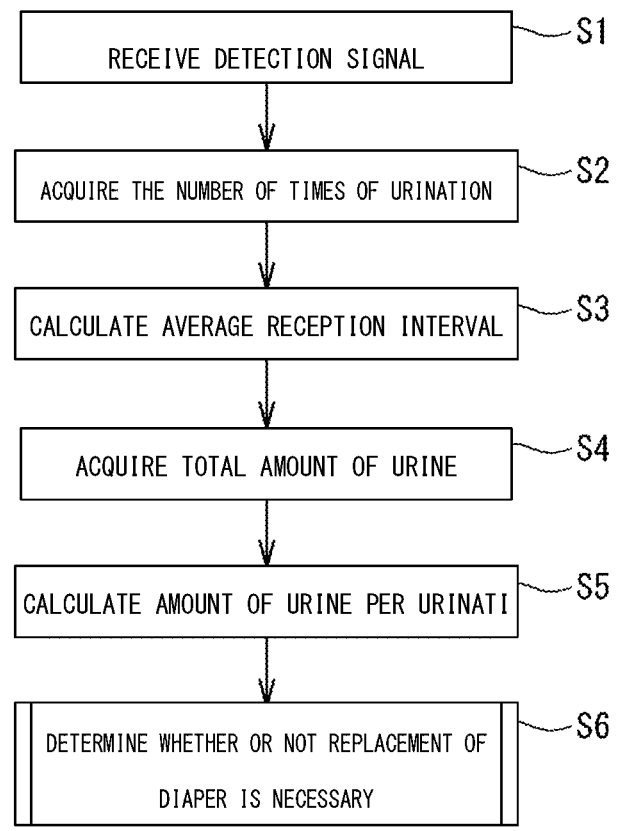
FIG. 11 is a flow chart showing the procedure of a process for assessment of necessity for replacement of the absorbent member.

The processing unit 16 in the replacement necessity assessment apparatus 10 determines the replacement time of the absorbent member 51 (the diaper 50) through the procedure shown in FIG. 11.

When the processing unit 16 has received a detection signal from the radio receiver 15 (step S1), the processing unit 16 acquires the number of times of urination, first (step S2). The number of times of urination can be acquired by measuring the timing when the detection signal has been received for the first time and the timing when the reception interval has changed, as shown in FIG. 5.

Then, the processing unit 16 calculates the average reception interval of the detection signal for each urination (step S3). The average reception interval can be the average of the reception intervals of the detection signal received during one hour, for example.

The processing unit 16 obtains the total amount of urine that corresponds to a range of the reception interval according to Table 1 described above (step S4). Specifically, in a case where the number of times of urination is one, the processing unit 16 obtains the total amount of urine based on the left column in Table 1, and in a case where the number of times of urination is two or greater, the processing unit 16 obtains the total amount of urine based on the right column in Table 1.

Next, the processing unit 16 calculates the amount of urine per urination (step S5). For example, in a case where the number of times of urination is one, the processing unit 16 sets the total amount obtained in step S4 as the amount per urination. In a case where the number of times of urination is two or greater, the processing unit 16 subtracts, from the total amount obtained in step S4, the total amount obtained for the immediately-preceding urination, thereby obtaining the amount per urination.

By use of the number of times of urination acquired in step S2 and the amount of urine per urination obtained in step S5, the processing unit 16 assesses necessity for replacement of the diaper 50 (step S6).

[Details of Replacement Necessity Assessment]

Figure 12:
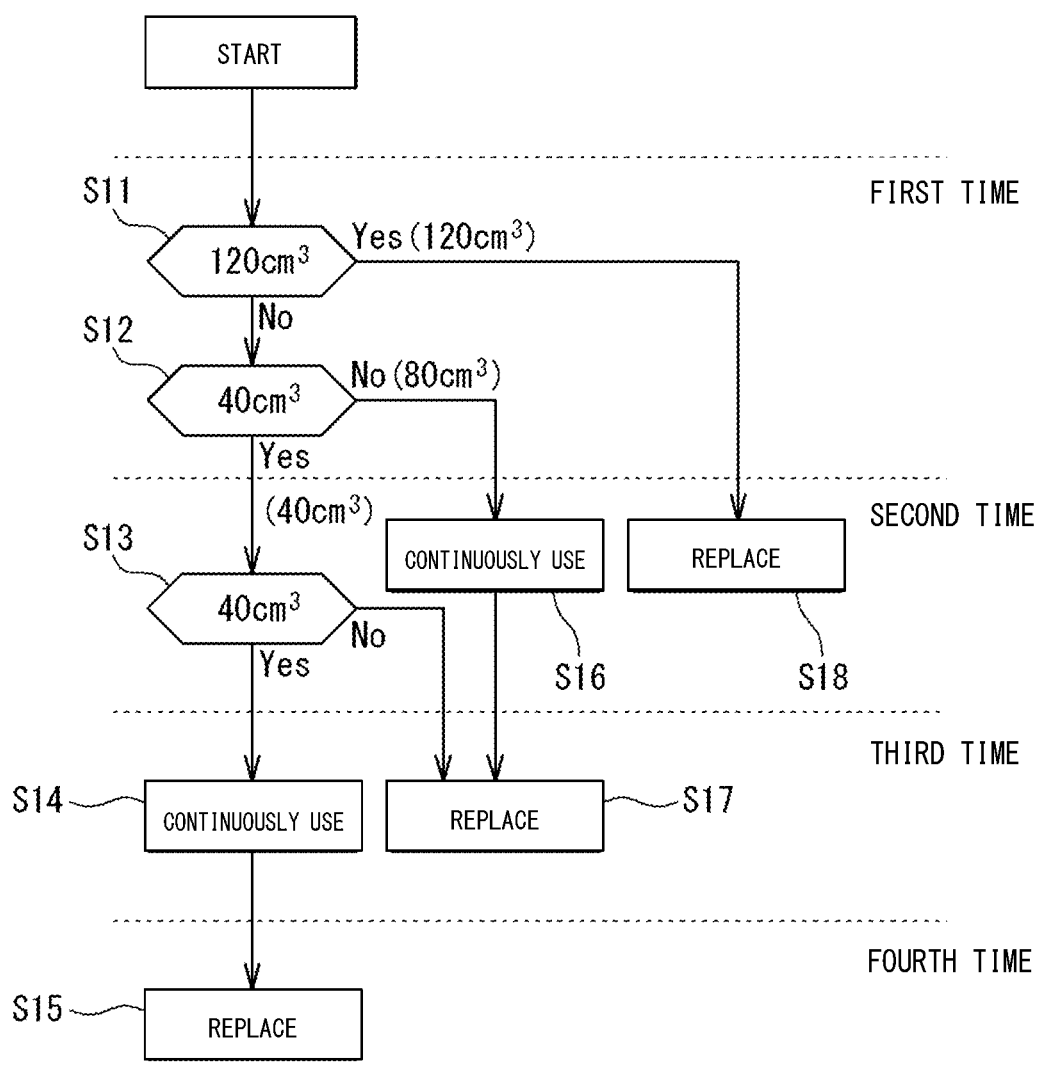
FIG. 12 is a flow chart showing in a more detailed manner the procedure of assessment of necessity for replacement of the absorbent member.

FIG. 12 is a flow chart showing in a more detailed manner the procedure of assessment of necessity for replacement of the diaper 50.

(First Urination)

In a case of the first urination, the processing unit 16 determines whether or not the amount of urine per urination is 120 cm$^3$ (step S11). When the determination result is positive (Yes), the processing unit 16 advances the process to step S18, and when the determination result is negative (No), the processing unit 16 advances the process to step S12. When the determination result is positive, the amount of urine per urination is fixed as 120 cm$^3$.

In step S12, the processing unit 16 determines whether or not the amount of urine per urination is 40 cm$^3$. When the determination result is positive (Yes), the processing unit 16 advances the process to step S13, and when the determination result is negative (No), the processing unit 16 advances the process to step S16. When the determination result is positive, the amount of urine per urination is fixed as 40 cm$^3$. When the determination result is negative, the amount of urine per urination is fixed as 80 cm$^3$.

(Second Urination)

Next, the processing unit 16 performs determination on the second urination. When the amount of urine of the first urination has been 40 cm$^3$, the processing unit 16 determines, in step S13, whether or not the amount of urine in the second urination is 40 cm$^3$. When the determination result is positive (Yes), the processing unit 16 advances the process to step S14, and when the determination result is negative (No), the processing unit 16 advances the process to step S17. When the determination result is positive, the amount of urine per urination is fixed as 40 cm$^3$. When the determination result is negative, the amount of urine per urination is fixed as 80 cm$^3$ or 120 cm$^3$.

In a case where the amount of urine at the first urination has been 80 cm$^3$, when the processing unit 16 has detected the second urination, the processing unit 16 determines, in step S16, that the diaper can be continuously used irrespective of the amount thereof. This is because, as shown in FIG. 9, the urine leakage state at the time when a unit amount of 80 cm$^3$ of urine has been infused and then a further 80 cm$^3$ of urine has been infused (at the time when the total amount is 160 cm$^3$), and the urine leakage state at the time when 80 cm$^3$ of urine has been further infused (at the time when the total amount is 240 cm$^3$) are taken into consideration. That is, even if the amount of urine at the second urination has been 80 cm$^3$ (total amount: 160 cm$^3$), the leakage from the diaper 50 is little. Hence it is considered that the leakage does not give discomfort to the user, and it is not necessary to replace the diaper immediately. Even if the amount of urine in the second urination has been 120 cm$^3$ (total amount: 200 cm$^3$), it is considered that the leakage amount is smaller than when the total amount is 240 cm$^3$, and thus, it is not necessary to replace the diaper immediately.

In a case where the amount of urine of the first urination has been 120 cm$^3$, as shown in FIG. 12, the processing unit 16 makes a determination that replacement of the diaper is necessary upon detection of the second urination in step S18. This determination is made based on the following: as shown in FIG. 9, after a unit amount of 120 cm$^3$ of urine has been infused and then 120 cm$^3$ of urine has been further infused (total amount: 240 cm$^3$), a large amount of urine leakage is caused. In addition, this determination is made based on the following: when a case where 40 cm$^3$ of urine has been infused in the state where the total amount is 120 cm$^3$ is taken into consideration with reference to the case of the unit amount of 40 cm$^3$, even if the total amount is 160 cm$^3$, there is a possibility that leakage occurs to an extent that would require replacement. Further, this determination is made based on the following: in a case where 80 cm$^3$ of urine has been further infused in the state where the total amount is 120 cm$^3$, the amount of leakage is considered to be further increased.

In step S18 shown in FIG. 12, the processing unit 16 also performs notification that replacement of the diaper is necessary. For this notification, for example, an alarm sound representing diaper replacement can be emitted from a speaker serving as the output unit 26. Alternatively, a display that diaper replacement is necessary can be displayed on a monitor serving as the output unit 26.

(Third Urination)

In a case where the amount of urine has been 40 cm$^3$ for each of the first urination and the second urination, when the processing unit 16 has detected the third urination, the processing unit 16 determines, in step S14, that the diaper can be continuously used irrespective of the amount thereof. This is because, as shown in FIG. 9, when a unit amount of 40 cm$^3$ of urine has been infused twice and then 40 cm$^3$ of urine has been further infused (total amount: 120 cm$^3$), the urine leakage is very little. Accordingly, even if 80 cm$^3$ or 120 cm$^3$ of urine has been infused (total amount: 160 cm$^3$ or 200 cm$^3$), it is considered that the leakage does not occur to an extent that would require replacement.

In a case where the amount of urine at the first urination has been 40 cm$^3$, and the amount of urine at the second urination has been 80 cm$^3$ or 120 cm$^3$, the processing unit 16 makes a determination that replacement of the diaper is necessary upon detection of the third urination in step S17. This is because, in this case, the total amount after the third urination becomes at least 160 cm$^3$, and it is considered that the urine leakage state at this time becomes an intermediate state between the state when urine has been infused four times by a unit amount of 40 cm$^3$ and the state when urine has been infused twice by a unit amount of 80 cm$^3$ in FIG. 9. Accordingly, there is a possibility that leakage from the diaper has occurred to an extent that would require replacement. Also, in step S17, notification that replacement of the diaper 50 is necessary is performed.

(Fourth Urination)

In a case where the amount of urine has been 40 cm$^3$ for each of the first urination and the second urination, and the third urination has been further performed, the processing unit 16 determines that replacement of the diaper is necessary upon detection of the fourth urination. Then, notification that replacement of the diaper 50 is necessary is also performed.

In step S13, in a case where the amount of urine has been 40 cm$^3$ for each of the first urination and the second urination, it has been determined, at the stage of the second urination that: the diaper is continuously used at the third urination; and diaper replacement is performed at the fourth urination. Therefore, in steps S14 and S15, the substantial determination process is not performed. This also applies to the procedure from step S12 to steps S16 and S17. In the procedure from step S11 to step S18, it has been determined, at the stage of the first urination, that diaper replacement is performed at the second urination. In this manner, at a stage corresponding to a number of times of urination before the number of times of urination that requires actual diaper replacement, the processing unit 16 makes a determination that replacement is to be necessary. Accordingly, at the timing when it is detected that urination has been performed the number of times that would require actual replacement, it is possible to instantly perform notification or the like that replacement is necessary, without performing calculation of the average of the reception intervals, acquisition of the total amount of urine, or the like. Therefore, it is possible to prevent continuous wearing of the diaper 50 in a state where urine has leaked from the absorbent member 51.

As described above, the replacement necessity assessment apparatus 10 of the present invention can detect that urine has been absorbed in the absorbent member 51 based on the detection signal according to the power generation amount by the power generator 11. Accordingly, it is not necessary to provide a sensor or the like that detects urine, separately from the power generator 11, and it is possible to reduce the number of components and simplify the structure. By using the parameters (the number of times of urination, the amount of urine per urination) regarding the amount of liquid acquired based on the detection signal, it is possible to assess necessity for replacement based on the amount of liquid absorbed in the absorbent member 51.

In the course of assessment of necessity for replacement of the absorbent member 51, the replacement necessity assessment apparatus 10 detects the amount of urine (liquid) absorbed in the absorbent member 51, such as the total amount of urine absorbed in the absorbent member 51, and the infused amount of urine per urination, for example. Hence the replacement necessity assessment apparatus 10 also serves as a liquid amount detection apparatus which detects the amount of liquid absorbed in the absorbent member 51, or an information acquisition apparatus which acquires information about the amount of liquid absorbed in the absorbent member 51.

[Verification Experiment]

The inventors of the present application performed a verification experiment as to whether or not the assessment procedure shown in FIG. 12 was appropriate. In this verification experiment, while actual urination is assumed and the amount per infusion is changed in a plurality of patterns, urine (artificial urine) was infused into a diaper 50 a plurality of times, and it is verified whether or not the actual urine leakage state in the diaper and the assessment of the necessity for diaper replacement match each other.

In the present experiment, urine was infused in the four patterns A to D shown in Table 2 below. For each pattern, the total amount is 240 cm$^3$. For each pattern, urine was infused every one hour.

TABLE 2

| Urine loading (urination) pattern | Loading amount (urination amount) of urine (cm$^3$/h) | | | | | |
|---|---|---|---|---|---|---|
| | First time | Second time | Third time | Fourth time | Fifth time | Sixth time |
| A | 40 | 40 | 40 | 40 | 40 | 40 |
| B | 40 | 40 | 80 | 40 | 40 | |
| C | 80 | 120 | 40 | | | |
| D | 120 | 80 | 40 | | | |

Figure 13:
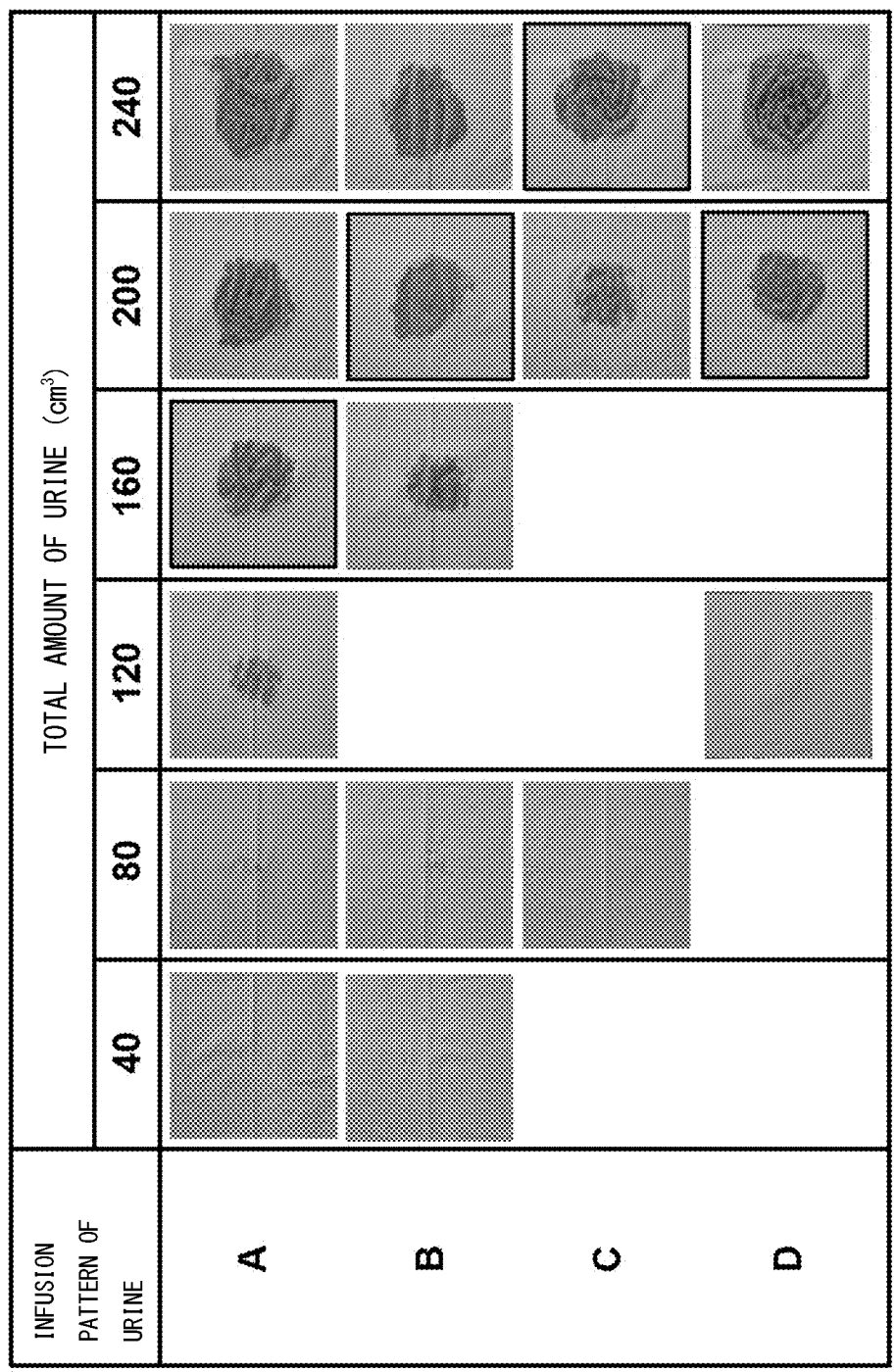
FIG. 13 shows images of the urine leakage state when urine was infused a plurality of times in a plurality of patterns.
Figure 14A:
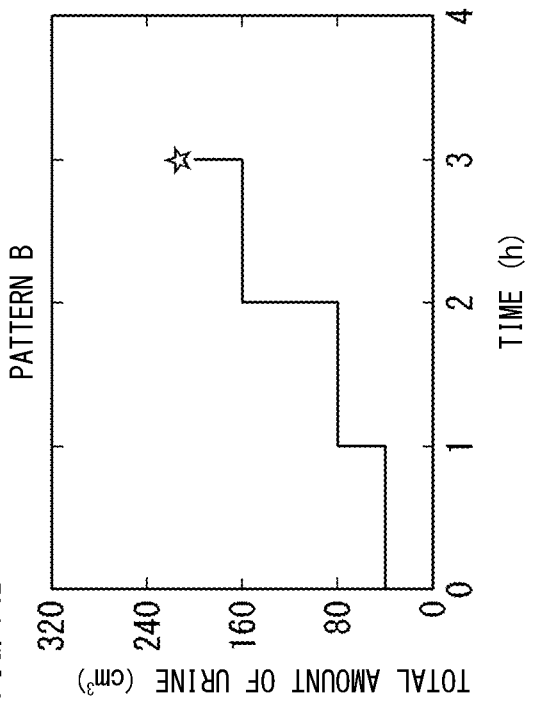
FIG. 14A is a graph showing the replacement time acquired by use of the procedure shown in FIG. 12 when urine has been infused a plurality of times in a pattern A shown in FIG. 13, together with the relationship between time and the total amount of urine.
Figure 14B:
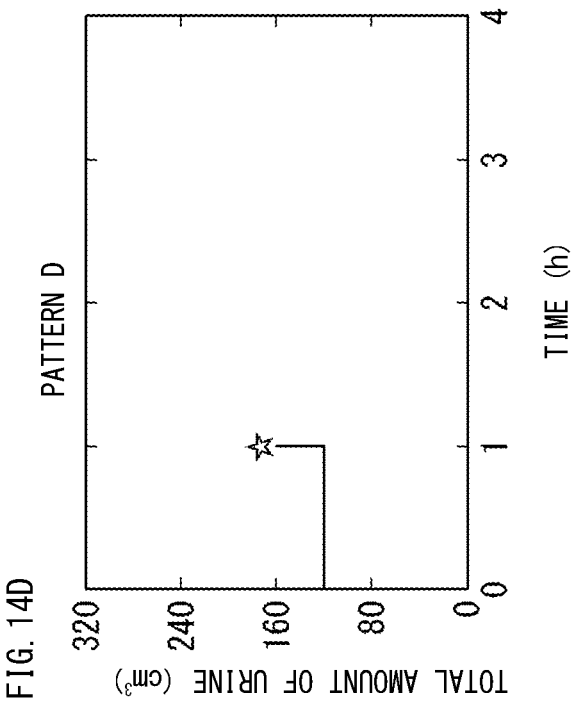
FIG. 14B is a graph showing the replacement time acquired by use of the procedure shown in FIG. 12 when urine has been infused a plurality of times in a pattern B shown in FIG. 13, together with the relationship between time and the total amount of urine.
Figure 14C:
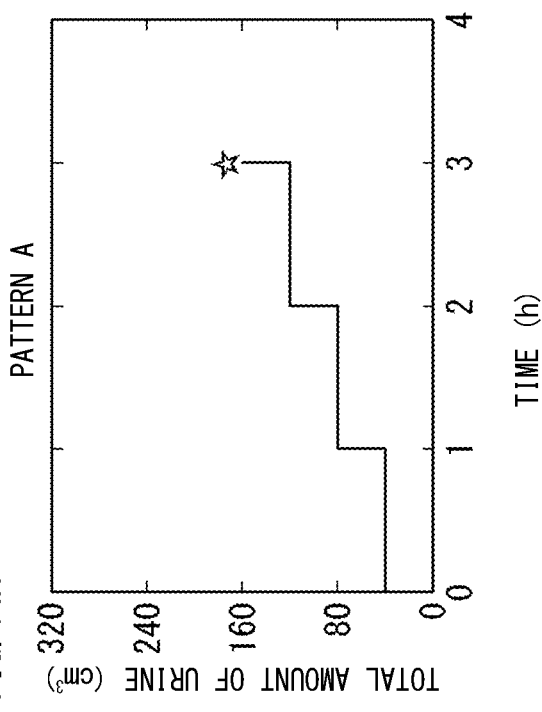
FIG. 14C is a graph showing the replacement time acquired by use of the procedure shown in FIG. 12 when urine has been infused a plurality of times in a pattern C shown in FIG. 13, together with the relationship between time and the total amount of urine.
Figure 14D:
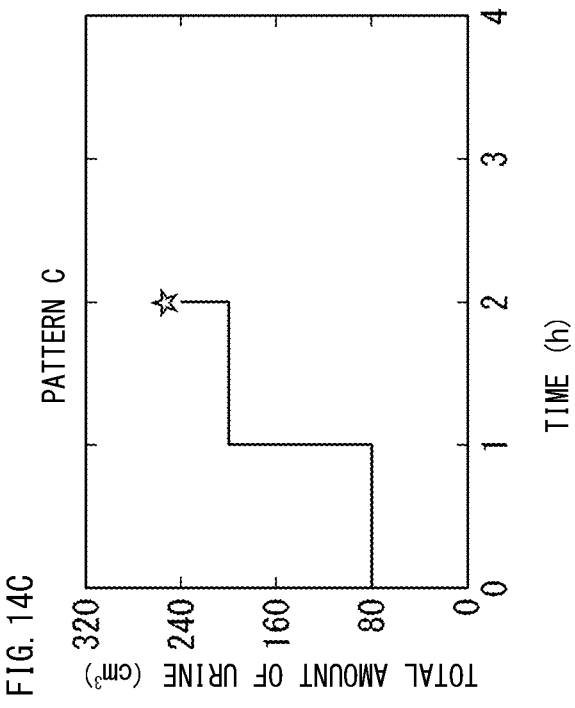
FIG. 14D is a graph showing the replacement time acquired by use of the procedure shown in FIG. 12 when urine has been infused a plurality of times in a pattern D shown in FIG. 13, together with the relationship between time and the total amount of urine.

FIG. 13 shows images of the urine leakage states in the plurality of patterns A to D. FIG. 14 shows the replacement time (indicated by a star symbol) acquired by use of the procedure shown in FIG. 12, together with the relationship between time and the total amount of urine.

In FIG. 14, the replacement time of the absorbent member is determined to be at the fourth time in the case of the patterns A, B; is determined to be at the third time in the case of the pattern C; and is determined to be at the second time in the case of the pattern D. When the actual urine leakage state of the diaper is confirmed with reference to FIG. 13, a large amount of urine leakage is observed at the fourth infusion of urine in the case of the patterns A, B; at the third infusion of urine in the case of the pattern C; and the second infusion of urine in the case of the pattern D, where diaper replacement is actually necessary. Accordingly, it has been confirmed that the procedure shown in FIG. 12 can appropriately determine the replacement time of the diaper.

Another Embodiment

Figure 15:
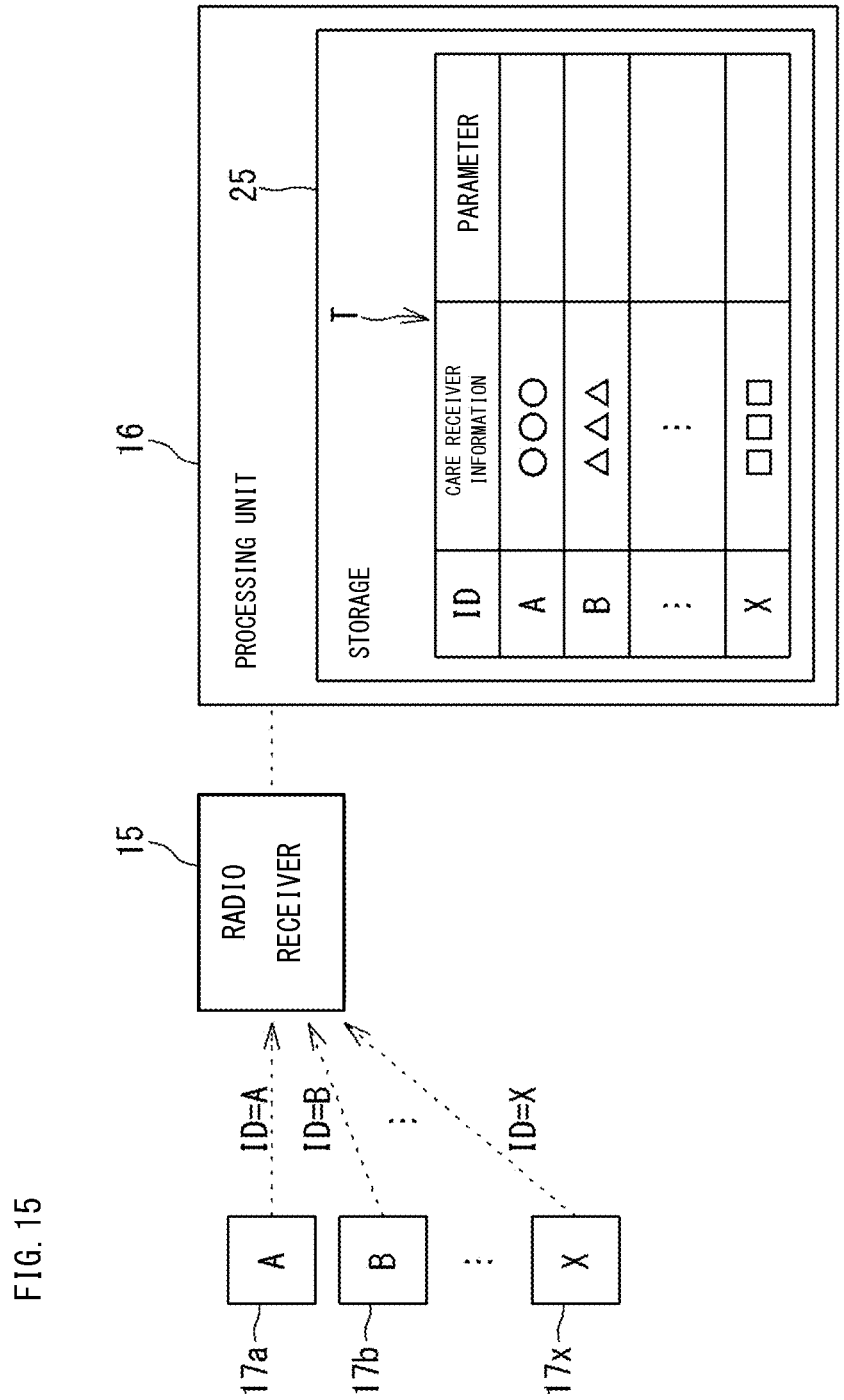
FIG. 15 is a diagram describing a replacement time assessment apparatus for an absorbent member according to another embodiment.

FIG. 15 is a configuration diagram showing a replacement necessity assessment apparatus (information acquisition apparatus) according to another embodiment. The replacement necessity assessment apparatus 10 includes: a plurality of sensor units 17a, 17b, . . . 17x; the radio receiver 15; and the processing unit 16. Each sensor unit 17a, 17b, . . . 17x includes the power generator 11, the power storage 12, the intermittent power supply 13, and the radio transmitter 14, similar to the above embodiment (FIG. 2). The plurality of sensor units 17a, 17b, . . . 17x are respectively provided in disposable diapers worn by a plurality of care receivers in a nursing facility, for example.

Each sensor unit 17a, 17b, . . . 17x has an identifier (ID) A, B, . . . X that has been individually provided. The radio transmitter 14 of each sensor unit 17a, 17b, . . . 17x transmits information of the identifier A, B, . . . X together with a detection signal. The radio receiver 15 receives the detection signal having attached thereto the identifier A, B, . . . X transmitted from a corresponding sensor unit 17a, 17b, . . . 17x, and sends the detection signal to the processing unit 16.

The storage 25 of the processing unit 16 has stored therein a table T in which the identifier A, B, . . . X provided to a corresponding sensor unit 17a, 17b, . . . 17x is associated with information (name, room number, bed position, etc.) of a corresponding care receiver who is wearing a disposable diaper provided with the sensor unit 17a, 17b, . . . 17x. By referring to the identifier of the detection signal transmitted from the radio receiver 15, the processing unit 16 determines from which sensor unit 17a, 17b, . . . 17x the detection signal has been transmitted. Then, based on the reception interval of the detection signal and change in the reception interval, the processing unit 16 can classify parameters such as the timing of urination, the number of times of urination, and the amount of urine (the total amount or the amount per urination) for each identifier A, B, . . . X and store the classified parameters in the storage. Therefore, assessment on whether or not replacement of the disposable diaper is necessary, detection of whether or not urination has been performed, detection of the amount of urine, and the like can be performed for each care receiver.

The present embodiment thereby discloses a liquid detection system that has the following features.

That is, the liquid detection system includes:

a power generator configured to perform power generation as a result of contact with liquid absorbed in an absorbent member;

a signal output unit configured to output a detection signal in accordance with the power generation; and a processing unit configured to detect, based on the detection signal, that the liquid has been absorbed.

The liquid detection system further includes:

a plurality of sensor units each including the power generator and the signal output unit, wherein the processing unit distinguishes the detection signal for each sensor unit and detects that liquid has been absorbed.

In the liquid detection system, the processing unit includes a storage that stores therein an identifier provided to each sensor unit, in association with information that specifies a position (including a place or a person) at which the power generator of the sensor unit has been attached.

For example, if the power generator of the sensor unit is installed together with an absorbent member, at a plurality of locations in a pipe in which liquid flows, this liquid detection system can be caused to function as a leakage detection system that detects the presence/absence of leakage of the liquid from the pipe, or a leakage location. In this case, in the table T shown in FIG. 15, information about the installation location of the power generator of the sensor unit 17a, 17b, . . . 17x is stored in a state of being associated with the identifier (ID) A, B, . . . X.

The present invention is not limited to the above-described embodiment, and changes can be made within the scope of the present invention described in the claims. For example, the following embodiment can be employed.

(1) A specific procedure of determining whether or not replacement of a diaper is necessary is not limited to the above-described embodiments, and changes can be made as appropriate. For example, in the procedure shown in FIG. 12, when the amount of first urination is 120 $cm^3$, replacement of the diaper is set to be necessary irrespective of the amount of urine at the second urination (see step S18). However, limited to a case where the amount of urine at the second urination is 40 $cm^3$, it is considered that the amount of urine leakage is not so large, and thus, it may be determined that continuous use of the diaper is allowed.

(2) In the above embodiment, the total amount of urine is acquired at a resolving power of 40 $cm^3$. However, not limited thereto, the total amount of urine may be acquired at a resolving power less than 40 $cm^3$ or greater than 40 $cm^3$.

(3) In the above embodiment, based on the number of times of urination and the amount of urine per urination, whether or not replacement of the diaper is necessary is determined. However, necessity for replacement of the diaper 50 may be assessed only based on the number of times of urination. For example, it can be determined that replacement of the diaper 50 is necessary at the timing when urine has been infused a predetermined number of times.

Alternatively, necessity for replacement of the diaper 50 can be assessed only based on the total amount of urine that has been infused into the diaper 50. For example, it can be assessed that replacement of the diaper 50 is necessary when the total amount of urine has reached a predetermined amount.

(4) In the above embodiment, the detection signal generated by the intermittent power supply 13 is transmitted by the radio transmitter 14, and whether or not replacement of the diaper is necessary is determined based on the detection signal received by the radio receiver 15. However, the intermittent power supply 13 and the processing unit 16 may be connected to each other with a cable, and the detection signal may be transmitted from the intermittent power supply 13 to the processing unit 16 via the cable.

(5) In the above embodiment, it is determined whether or not replacement of a diaper 50 having the absorbent member 51 built therein is necessary. However, not limited to the diaper 50, it may be determined whether or not replacement of excretion training pants, an incontinence brief, an absorbent pad, or the like is necessary. Further, the absorbent member 51 is not limited to an absorbent member that absorbs urine, but may be an absorbent member that absorbs liquid other than urine.

(6) The information acquisition apparatus of the above embodiment can be not only used in determining whether or not replacement of a disposable diaper or the like is necessary, but can be widely applied for grasping the amount of liquid absorbed in an absorbent member. For example, if the power generator of the sensor unit is attached to a plant or a culture medium for a plant, the information acquisition apparatus can be used as a cultivation management apparatus that detects the amount of water of a plant or a culture medium and that manages the supply time or the like of water or culture liquid.

REFERENCE SIGNS LIST

10: replacement necessity assessment apparatus
11: power generator
12: power storage (signal output unit)
13: intermittent power supply (signal output unit)
14: radio transmitter
15: radio receiver
16: processing unit
21: sheet-shaped electrode
26: output unit
50: disposable diaper
51: absorbent member

The invention claimed is:

1. A replacement necessity assessment apparatus for an absorbent member, the replacement necessity assessment apparatus comprising:
a power generator configured to generate power as a result of contact with liquid absorbed in the absorbent member, and of which power generation amount changes in accordance with an amount of the liquid;
a power storage configured to be applied electromotive force generated by the power generator and to store electric charge;
an intermittent power supply configured to receive power when a predetermined amount of electric charge has been stored in the power storage and intermittently generate and output a detection signal every time power is supplied from the power storage; and
a processing unit configured to acquire a parameter regarding the amount of the liquid based on the time interval at which the detection signal is outputted by the intermittent power supply, the processing unit configured to determine, based on the parameter, whether or not replacement of the absorbent member is necessary.

2. The replacement necessity assessment apparatus for the absorbent member according to claim 1, wherein
the parameter includes the number of times the liquid has been infused into the absorbent member.

3. The replacement necessity assessment apparatus for the absorbent member according to claim 1, wherein
the parameter includes an amount of the liquid per infusion that has been infused into the absorbent member.

4. The replacement necessity assessment apparatus according to claim 1, wherein
on the basis of a change in the time interval at which the detection signal is outputted by the intermittent power supply, the processing unit acquires, as the parameter, the number of times the liquid has been infused into the absorbent member.

5. The replacement necessity assessment apparatus according to claim 4, wherein
the time interval at which the detection signal is outputted is associated with the amount of the liquid for each predetermined range.

6. The replacement necessity assessment apparatus according to claim 5, wherein
the predetermined range is different in accordance with the number of times the liquid has been infused into the absorbent member.

7. The replacement necessity assessment apparatus according to claim 1, wherein
on the basis of the time interval at which the detection signal is outputted by the intermittent power supply, the processing unit acquires, as the parameter, an amount of the liquid per infusion that has been infused into the absorbent member.

8. The replacement necessity assessment apparatus according to claim 1, wherein
the processing unit acquires the parameter based on an average value of the time interval at which the detection signal is outputted by the intermittent power supply.

9. The replacement necessity assessment apparatus according to claim 1, further comprising:
a radio transmitter configured to wirelessly transmit the detection signal; and
a radio receiver configured to receive the detection signal transmitted, wherein
the processing unit acquires the parameter based on the detection signal received by the radio receiver.

10. The replacement necessity assessment apparatus according to claim 1, wherein
at a stage corresponding to a number of times before the number of times of infusion of the liquid that requires replacement of the absorbent member, the processing unit determines that replacement of the absorbent member is to be necessary at a subsequent infusion or thereafter.

11. The replacement necessity assessment apparatus according to claim 1, wherein
the power generator includes a sheet-shaped electrode that consists only of carbon or a sheet-shaped electrode that contains the carbon.

12. The replacement necessity assessment apparatus according to claim 11, wherein
the sheet-shaped electrode is disposed at a side opposite to a side where the liquid is infused into the absorbent member.

13. An apparatus comprising:
a power generator which is configured to generate power as a result of contact with liquid absorbed in an absorbent member, and of which power generation amount changes in accordance with an amount of the liquid;
a power storage configured to be applied electromotive force generated by the power generator and to store electric charge; and
an intermittent power supply configured to receive power when a predetermined amount of electric charge has been stored in the power storage and intermittently generate and output a detection signal every time power is supplied from the power storage.

14. The apparatus according to claim 13, further comprising
a processing unit configured to acquire a parameter regarding the amount of the liquid based on the time interval at which the detection signal is outputted.

15. A replacement necessity assessment apparatus for an absorbent member, the replacement necessity assessment apparatus comprising:
 a power generator configured to generate power as a result of contact with liquid absorbed in the absorbent member, and of which power generation amount changes in accordance with an amount of the liquid;
 a signal output unit configured to output a detection signal according to the power generation amount; and
 a processing unit configured to acquire a parameter that includes an amount of the liquid per infusion that has been infused into the absorbent member based on an average value of the time interval at which the detection signal is outputted by the signal output unit, the processing unit configured to determine, based on the parameter, whether or not replacement of the absorbent member is necessary.

16. The replacement necessity assessment apparatus according to claim 15, wherein
 the time interval at which the detection signal is outputted is associated with the amount of the liquid for each predetermined range.

17. The replacement necessity assessment apparatus according to claim 15, further comprising:
 a radio transmitter configured to wirelessly transmit the detection signal; and
 a radio receiver configured to receive the detection signal transmitted, wherein
 the processing unit acquires the parameter based on the detection signal received by the radio receiver.

18. The replacement necessity assessment apparatus according to claim 15, wherein
 at a stage corresponding to a number of times before the number of times of infusion of the liquid that requires replacement of the absorbent member, the processing unit determines that replacement of the absorbent member is to be necessary at a subsequent infusion or thereafter.

19. The replacement necessity assessment apparatus according to claim 15, wherein
 the power generator includes a sheet-shaped electrode that consists only of carbon or a sheet-shaped electrode that contains the carbon.

* * * * *